United States Patent [19]

Romine

[11] 3,964,993

[45] June 22, 1976

[54] REMOVAL OF HF FROM THE SLUDGE RESULTING FROM THE TREATMENT OF A HYDROCARBON

[75] Inventor: Hugh E. Romine, Ponca City, Okla.

[73] Assignee: Continental Oil Company, Ponca City, Okla.

[22] Filed: Jan. 23, 1975

[21] Appl. No.: 543,592

[52] U.S. Cl.............................. 208/13; 260/683.48
[51] Int. Cl.² ......................................... C10G 17/00
[58] Field of Search................... 208/13; 260/683.48

[56] References Cited
UNITED STATES PATENTS 2,413,310  12/1946  Bloch ................................. 208/13

*Primary Examiner*—Herbert Levine
*Attorney, Agent, or Firm*—Bayless E. Rutherford, Jr.

[57] ABSTRACT

A process for removing HF (hydrogen fluoride) from the sludge resulting from the HF treatment of a hydrocarbon is disclosed. The process comprises concurrently treating the sludge with aqueous caustic and a liquid aromatic hydrocarbon.

4 Claims, No Drawings

REMOVAL OF HF FROM THE SLUDGE RESULTING FROM THE TREATMENT OF A HYDROCARBON

BACKGROUND

1. Field of the Invention

The invention is in the field of treating sludge resulting from the HF (hydrogen fluoride) treatment of hydrocarbons to remove residual HF therefrom.

2. General Background

Numerous processes are known for treating hydrocarbons with HF. Such processes include isomerization, alkylation, polymerization, desulfurization and reforming. Typically, these processes produce a sludge which contains residual HF. In order to upgrade the sludge to normal hydrocarbon value, it is necessary to eliminate or substantially reduce the HF content thereof. My invention is directed to the solution of this problem.

The hydrocarbon product of my invention is useful as a fuel oil.

3. Prior Art

A search of the prior art by a Washington searcher did not produce any art directly pertinent to the invention described herein. The search called attention to the following U.S. patents, which are of related interest:

U.S. Pat. No. 2,762,759 teaches that it is known to treat acid sludge, resulting from the treatment with sulfuric acid, with caustic soda. The method of the patent is directed to decomposing acid sludge, resulting from the treatment of a viscous hydrocarbon oil with sulfuric acid, by treatment with spent caustic, derived from the treatment of a straight-run petroleum distillate, and naphthenic acids.

U.S. Pat. No. 2,614,132 is directed to the recovery of drying oils from HF-hydrocarbon complexes (sludge) resulting from the treatment of a hydrocarbon with HF. Briefly, the process comprises many steps, one of which uses a light paraffinic oil as a diluent.

BRIEF SUMMARY OF THE INVENTION

Broadly stated, the present invention is directed to a process for removing HF (hydrogen fluoride) from the sludge, resulting from the HF treatment of hydrocarbons, wherein the process comprises concurrently treating the sludge with aqueous caustic and a liquid aromatic hydrocarbon.

More particularly, the process of the present invention comprises:

a. adding to the sludge, aqueous caustic and a liquid aromatic hydrocarbon, b. allowing the admixture of step (a) to form an aqueous phase and a hydrocarbon phase, and c. separating the aqueous phase and hydrocarbon phase.

DETAILED DESCRIPTION

Materials

The material which is subjected to treatment in my process is a by-product of various chemical and refining processes which involve treatment of hydrocarbons with HF. Typical HF-hydrocarbon processes include isomerization, polymerization, alkylation, desulfurization and reforming. A preferred material to be subjected to treatment in my process is the sludge resulting from HF alkylation processes. While I prefer the term "sludge", others have used other terms. For example, U.S. Pat. No. 2,614,132 uses the term "HF-hydrocarbon complexes." It is recognized that the sludge contains a considerable quantity of HF.

Knowing that an aqueous caustic solution is used in my process, any person skilled in the art can readily select a suitable caustic solution. By reason of cost and availability, the preferred material is an aqueous solution of sodium hydroxide. "Spent caustic" solutions resulting from various chemical and refining operations can, of course, be used. In addition to sodium hydroxide, other water-soluble alkali and alkaline earth metal hydroxides, carbonates and bicarbonates are suitable.

The concentration of the aqueous caustic solution can vary over a wide range. Usually, the amount of caustic in the aqueous solution will be in the range of about 1 to about 50 percent by weight. More usually, the amount of caustic will be in the range of about 2 to about 20 percent by weight.

Use of any significant amount of caustic will, of course, provide a reduction in the amount of HF present in the sludge. From a practical viewpoint, the amount of caustic usually is from about 1 to about 1000 times stoichiometric, based on the HF present in the sludge. More usually, on the same basis, the amount of caustic is from about 50 to about 500 times the stoichiometric requirement.

As noted hereinbefore, the important feature of my process is the use of a liquid aromatic hydrocarbon in conjunction with the aqueous caustic solution. Knowing this feature, any person skilled in the art can readily select a variety of suitable liquid aromatic hydrocarbons. Examples of suitable liquid aromatic hydrocarbon include benzene, the alkylated benzenes (e.g. toluene and xylene), naphthalene and alkylated naphthalenes. Suitable aromatic hydrocarbons are those boiling in the range of about 37 to about 320°C.

In addition to the foregoing, my process can use liquid diluents containing at least 10 weight percent of liquid aromatic hydrocarbons as defined. Preferably, the liquid diluent contains at least 30 weight percent, more preferably 50 weight percent, of liquid aromatic hydrocarbons. While the preferred liquid diluent is a hydrocarbon or mixture of hydrocarbons, other materials which are miscible with the aromatic hydrocarbon can be used.

Particularly suitable materials for use in my invention are refinery hydrocarbon streams containing a substantial amount of aromatics. One such material is referred to as light cycle oil. A typical light cycle oil has the following properties:

| | |
|---|---|
| Specific Gravity | 0.9346 |
| F.I.A. Analysis*, Vol. % | |
| Saturates | 21 |
| Olefins | 3 |
| Aromatics | 76 |
| D-86 Distillation, °C. | |
| IBP | 107 |
| 5% | 217 |
| 50% | 276 |
| 95% | 309 |
| EP | 315 |

*A.S.T.M. Method D-1319-70

The amount of liquid aromatic hydrocarbon or liquid diluent containing liquid aromatic hydrocarbon can vary over a wide range. Expressed as volume percent, based on the sludge, a suitable amount is about 1 to about 1000, more suitably the amount is about 5 to about 500, preferably the amount is about 50 to about 200. It naturally follows that use of a diluent containing a lower amount of aromatic hydrocarbon makes it desirable to use a larger amount of such material.

PROCESS CONDITIONS

Knowing the details of my invention as described hereinbefore, it is believed that any person skilled in the art can practice the invention without undue experimentation. Accordingly, the following description of process conditions is included solely to provide a complete teaching of my process.

Preferably, the liquid aromatic hydrocarbon is added to the sludge prior to adding the aqueous caustic solution.

The temperature of the admixture (sludge, liquid aromatic hydrocarbon and aqueous caustic solution) should be sufficient to allow complete mixing of the materials.

Agitation of the admixture is desirable to provide complete mixing. The amount of agitation can readily be determined by those skilled in the art.

Upon completion of agitation, the admixture is allowed to settle to form an aqueous phase and a hydrocarbon phase.

The aqueous phase and hydrocarbon phase are then separated. As is apparent to those skilled in the art, the hydrocarbon phase is the desired phase. The hydrocarbon phase is usable, as is, as a fuel oil. Or, if desired, it can be incorporated into an appropriate refinery stream, such as the gas oil stream.

In order to disclose the nature of the present invention still more clearly, the following examples, both illustrative and comparative, will be given. It is to be understood that the invention is not to be limited to the specific conditions or details set forth in these examples except insofar as such limitations are specified in the appended claims.

In the following examples the sludge employed was a by-product of a refinery alkylation process. It contained 800 ppm (parts per million) residual HF and had the following properties:

Viscosity: 1647.3 c.s. at 37.8°C.
Specific Gravity: 0.9224 at 15.6°C.

Examples 1–3 are comparative and show the effect of adding only aqueous caustic to the sludge. Four volumes (400%) of aqueous 5% (wt.) sodium hydroxide were used per volume of sludge. (The stoichiometric amount of caustic was 125). The agitation temperature, agitation time, split time (time required to form separate phases) and residual HF are shown in the table below.

TABLE I

| Example No | Agitation Temp. °C. | Agitation Time (Min) | Split Time (Min.) | Residual HF (ppm) |
|---|---|---|---|---|
| 1 | 42 | 1.5 | 0.5 | 430 |
| 2 | 54 | 15.0 | 0.3 | 90 |
| 3 | 4 | 15.0 | 0.8 | 450 |

Examples 4 and 5 are illustrative and show the effect of using an aromatic hydrocarbon, either alone or in admixture with a paraffinic hydrocarbon. The amount and concentration of aqueous caustic were the same as in Examples 1–3. Example 4 used 9 volumes (900%) of toluene per volume of sludge, while Example 5 used 0.1 volume (10%) of a 50/50 volume mixture of toluene and hexane. The sludge used was the same as used in Examples 1–3. The agitation temperature, agitation time, split time and residual HF are shown in the table below.

TABLE II

| Example No | Agitation Temp. °C. | Agitation Time (Min) | Split Time (Min.) | Residual HF (ppm) |
|---|---|---|---|---|
| 4 | 24 | 5.0 | 0.6 | <5 |
| 5 | 23 | 3.0 | 0.5 | 7 |

Examples 6–13 are both comparative and illustrative. All examples used four volumes (400%) of aqueous 5% (wt.) sodium hydroxide per volume of sludge. Example 6, which is comparative, did not use an aromatic hydrocarbon. Example 7, which is illustrative, used toluene. Examples 8–12, which are also illustrative, used a light cycle oil, of the type described previously herein. The agitation time was the same for all examples (3 minutes). The agitation temperature was similar in all runs (21°–22°C. room temperature). The split time was 1 minute or less. The sludge used was similar to that used in Examples 1–5 except that it contained 280 ppm of residual HF. The stoichiometric amount of caustic was 357.

TABLE III

| Example No | Volumes of Aromatic Hydrocarbon (a) | Residual HF (ppm) |
|---|---|---|
| 6 | none | 265 |
| 7 | 0.5 | 6 |
| 8 | 0.1 | 81 |
| 9 | 0.3 | 70 |
| 10 | 0.5 | 38 |
| 11 | 1 | 58 |
| 12 | 5 | 8 |

In all of the preceding examples, the value shown for the residual HF was based on unit volume of original sludge.

Having thus described the invention in detail, it will be understood by those skilled in the art that certain variations and modifications may be made without departing from the spirit and scope of the invention as defined herein and in the appended claims.

The invention having thus been described, what is claimed and desired to be secured by Letters Patent is:

1. A process for removing HF from the sludge resulting from the HF treatment of hydrocarbons, said process comprising:
   a. adding to the sludge, aqueous caustic and more than 10%, by volume, based on the sludge, of a liquid aromatic diluent containing at least 30 weight percent aromatics, to form an admixture,
   b. allowing the admixture of step (a) to form an aqueous phase and a hydrocarbon phase, and
   c. separating the aqueous phase and the hydrocarbon phase, said process being characterized further in that:
      a. the aqueous caustic solution contains from about 1 to about 50 weight percent caustic, and
      b. the amount and concentration of aqueous caustic are such as to provide an amount of caustic which is in the range of about 1 to about 1,000 times the stoichiometric requirement, based on the HF present in the sludge.

2. The process of claim 1 wherein the source of the liquid aromatic diluent is a light cycle oil.

3. The process of claim 1 wherein the sludge is a by-product of a refinery alkylation process.

4. The process of claim 2 wherein the sludge is a by-product of a refinery alkylation process.

* * * * *